(12) United States Patent
Wolleschensky et al.

(10) Patent No.: US 7,009,699 B2
(45) Date of Patent: Mar. 7, 2006

(54) METHOD FOR INVESTIGATING A SAMPLE

(75) Inventors: Ralf Wolleschensky, Schoeten (DE);
Bernhard Zimmermann, Potsdam
(DE); Sesbastian Tille, Pleasantville,
NY (US)

(73) Assignee: Carl Zeiss Jena GmbH, Jena (DE)

( * ) Notice: Subject to any disclaimer, the term of this patent is extended or adjusted under 35 U.S.C. 154(b) by 386 days.

(21) Appl. No.: 10/057,571

(22) Filed: Jan. 24, 2002

(65) Prior Publication Data

US 2003/0151741 A1 Aug. 14, 2003

(30) Foreign Application Priority Data

Oct. 16, 2001 (DE) .......................................... 101 51 217

(51) Int. Cl.
*G01N 21/64* (2006.01)

(52) U.S. Cl. .......................... 356/317; 356/72; 356/318; 356/328; 250/458.1

(58) Field of Classification Search .................. 356/72, 356/317, 318, 326, 328; 250/458.1, 459.1, 250/461.1, 461.2
See application file for complete search history.

(56) References Cited

U.S. PATENT DOCUMENTS

| 4,786,170 A | 11/1988 | Groebler |
| 5,192,980 A | 3/1993 | Dixon et al. |
| 5,418,371 A | 5/1995 | Aslund et al. |
| 5,859,700 A | 1/1999 | Yang |
| 5,871,628 A | * 2/1999 | Dabiri et al. ............... 204/461 |

FOREIGN PATENT DOCUMENTS

| DE | 198 29 981 A1 | 1/2000 |
| DE | 100 38 526 A | 2/2002 |

OTHER PUBLICATIONS

Lansford R, et al., "Resolution of Multiple Green Fluorescent Protein Color Variants and Dyes Using Two–photon Microscopy and Imaging Spectroscopy", Journal of Biomedical Optics, SPIE, Bellingham, WA, US, BD 6, Nr. 3, Jul., 2001. vol. 6 No. 3, pp. 311–318, XP–001117891.

Yang, M., et al., "Graphical User Interface for Single–Pixel Spectroscopy", Biotechnology et alia, Sep. 8, 2000, pp. 1–8, XP–002186905.

Youvan, et al., "Fluorescence Imaging Micro–Spectrophotometer (FIMS)", Biotechnology et alia, 1997, Kairos Scientific Inc., pp. 1–16. XP–002186906.

Robinson L, et al., "Confocal Microscopes Probe Biological Specimens", Laser Focus World, May, 1994, Tulsa, US, pp. 1–4, XP–002173906.

* cited by examiner

*Primary Examiner*—F. L. Evans
(74) *Attorney, Agent, or Firm*—Reed Smith LLP

(57) ABSTRACT

A method for investigating specimens, wherein a spectral splitting of the radiation coming from the specimen is carried out for specimen points or point distributions, for the operation of a laser scanning microscope or a fluorescence screening arrangement or a flow cylinder comprising the steps of generating a λ-stack so that the spectral distribution is measured by individual detection channels and storing the signals so as to be correlated to the detection signals with at least one of the spatial coordinates x, y and z and/or so as to be correlated to the measurement time t.

29 Claims, 18 Drawing Sheets

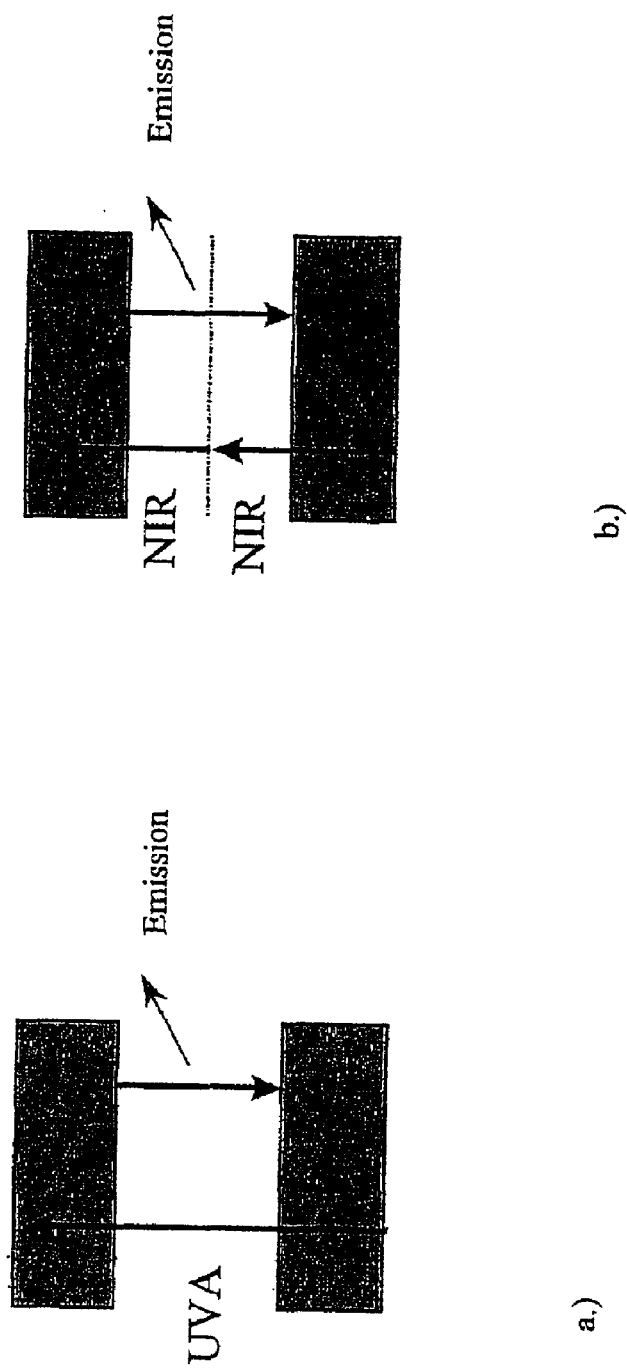
Figure: 1

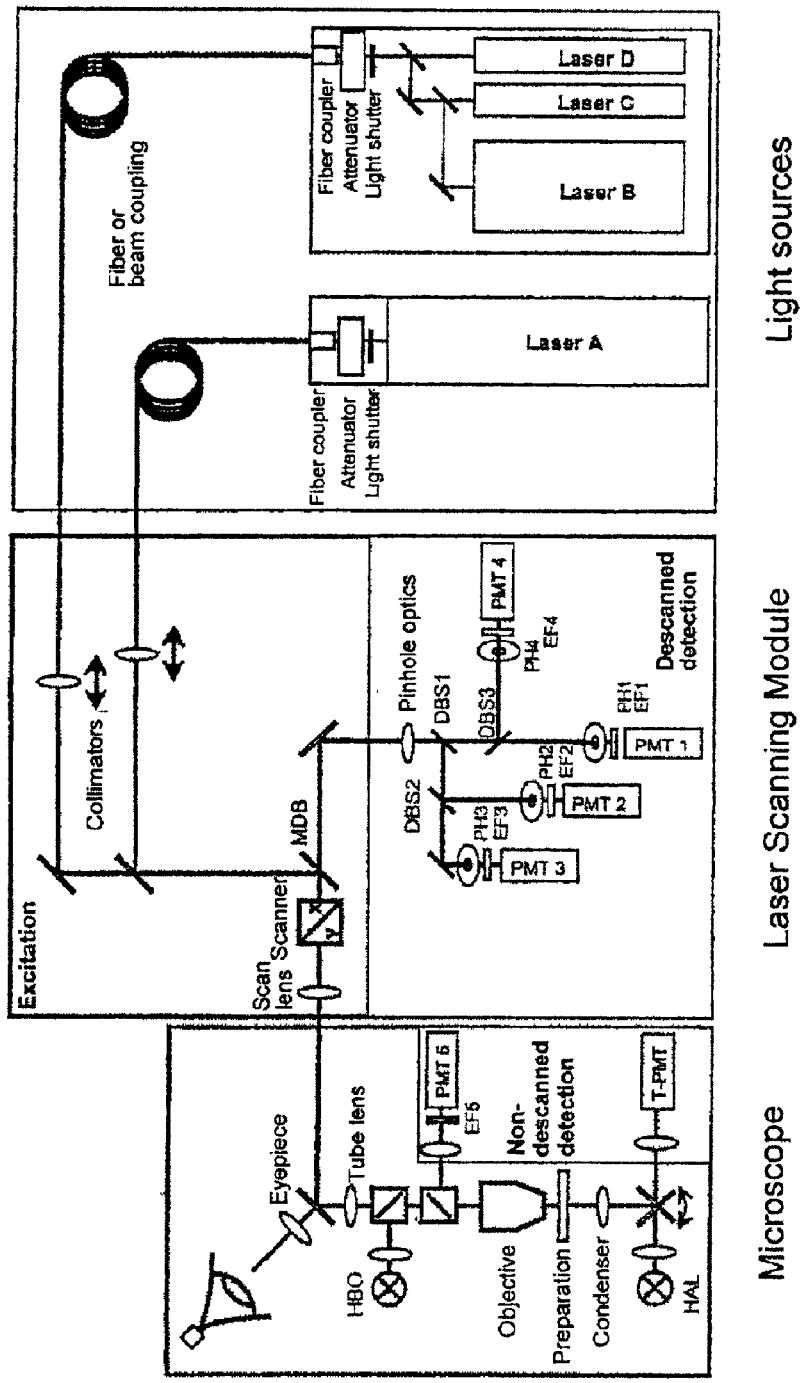
Figure: 2

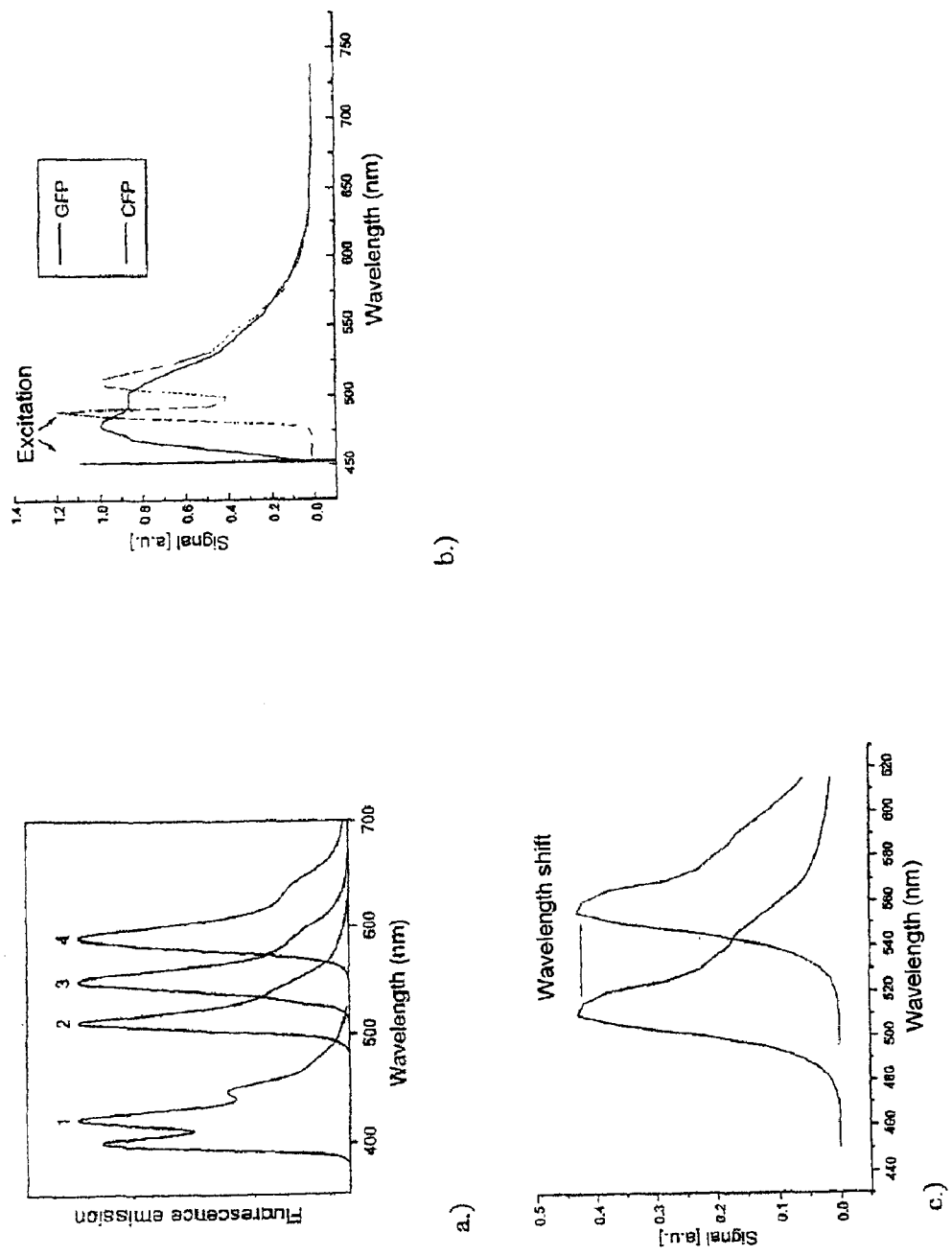
Figure: 3

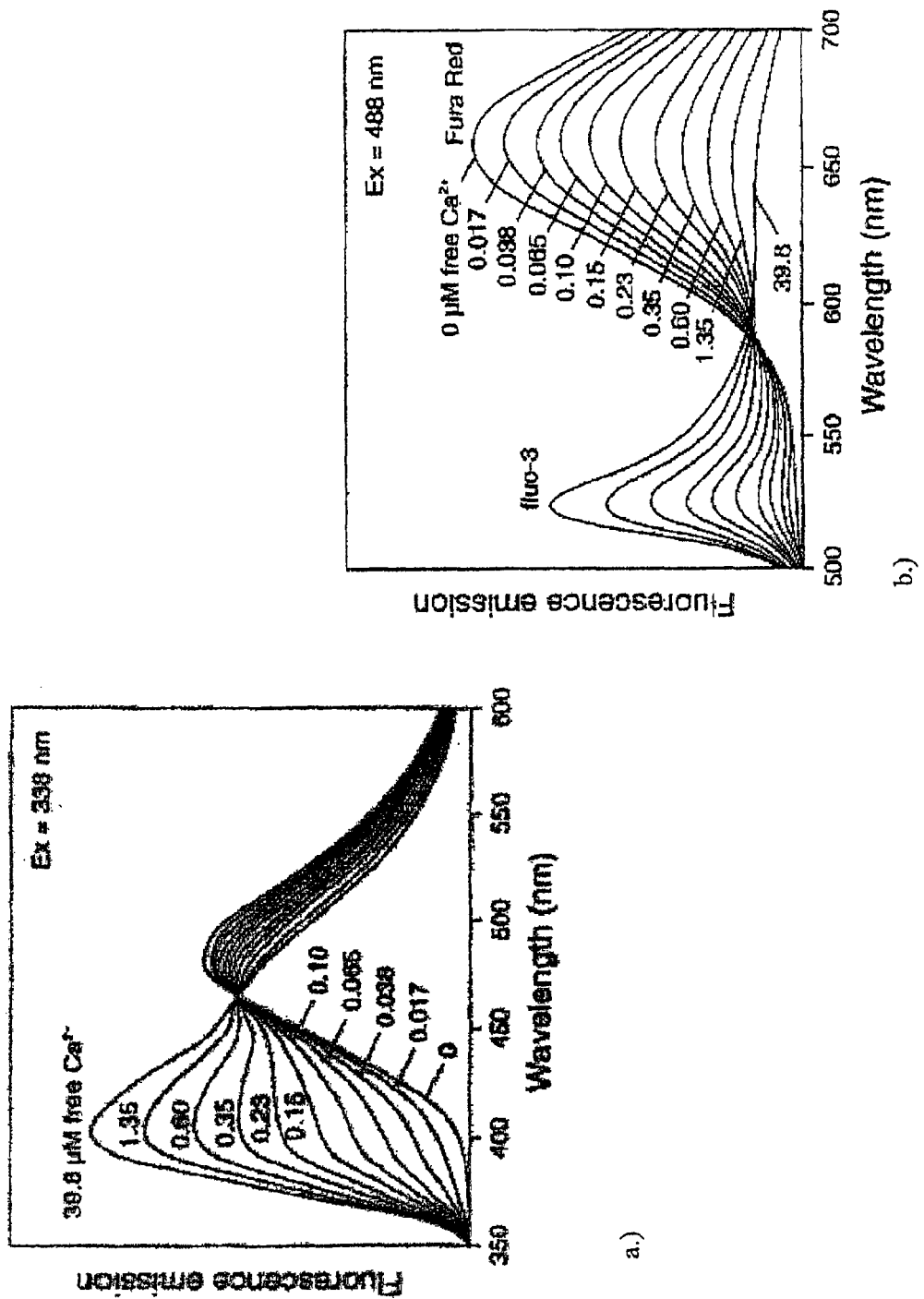
Figure: 4

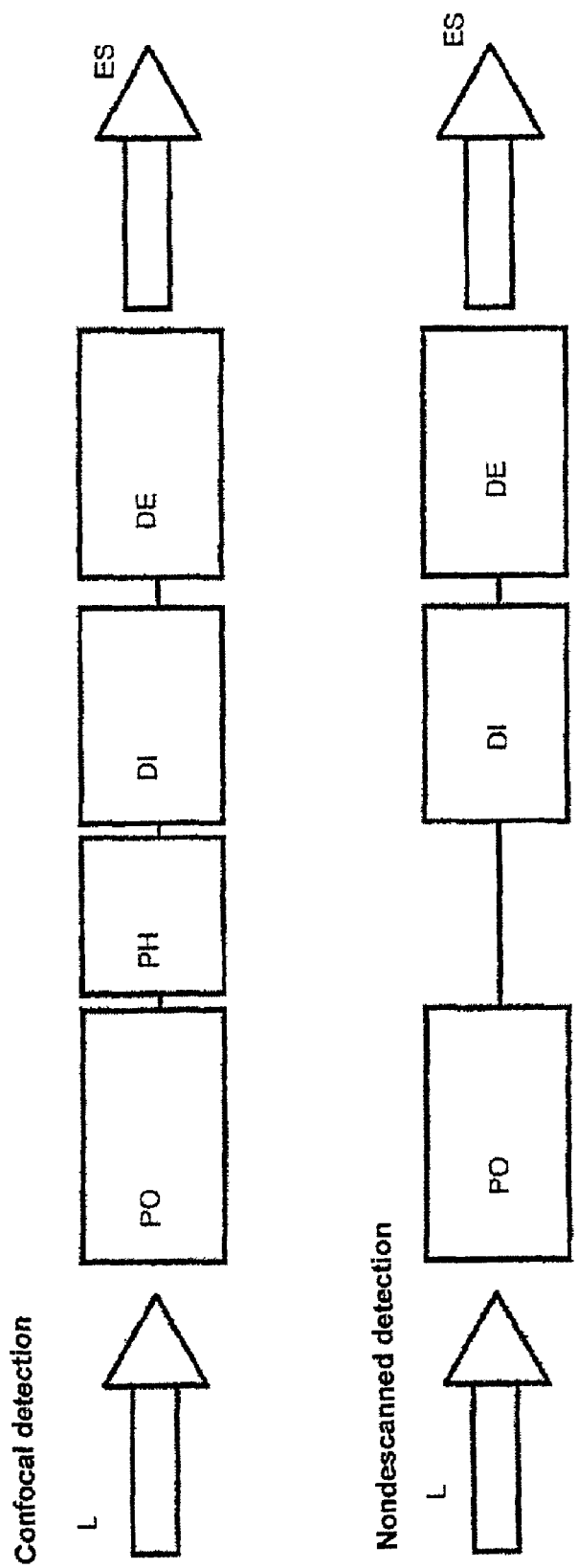
Figure: 5

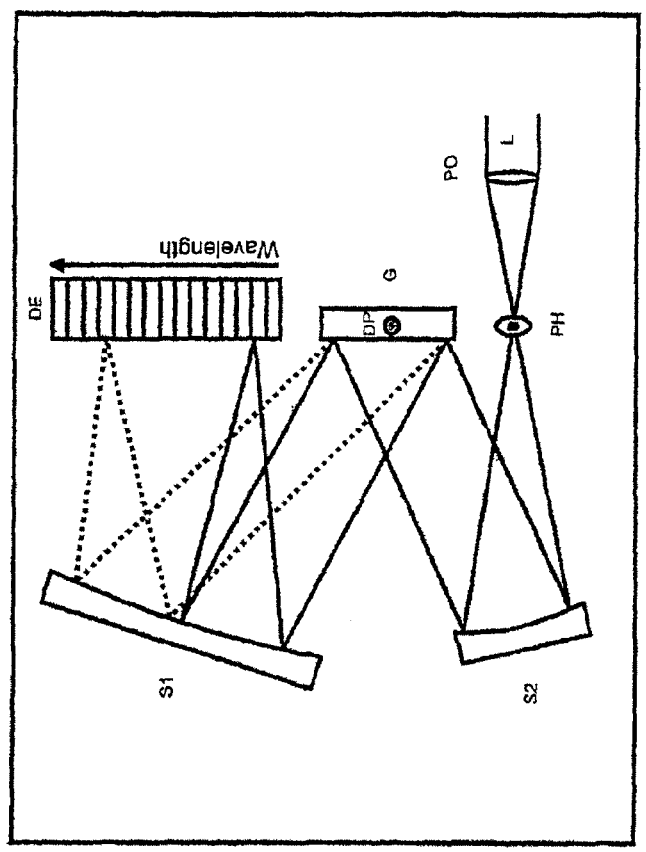
Figure: 6

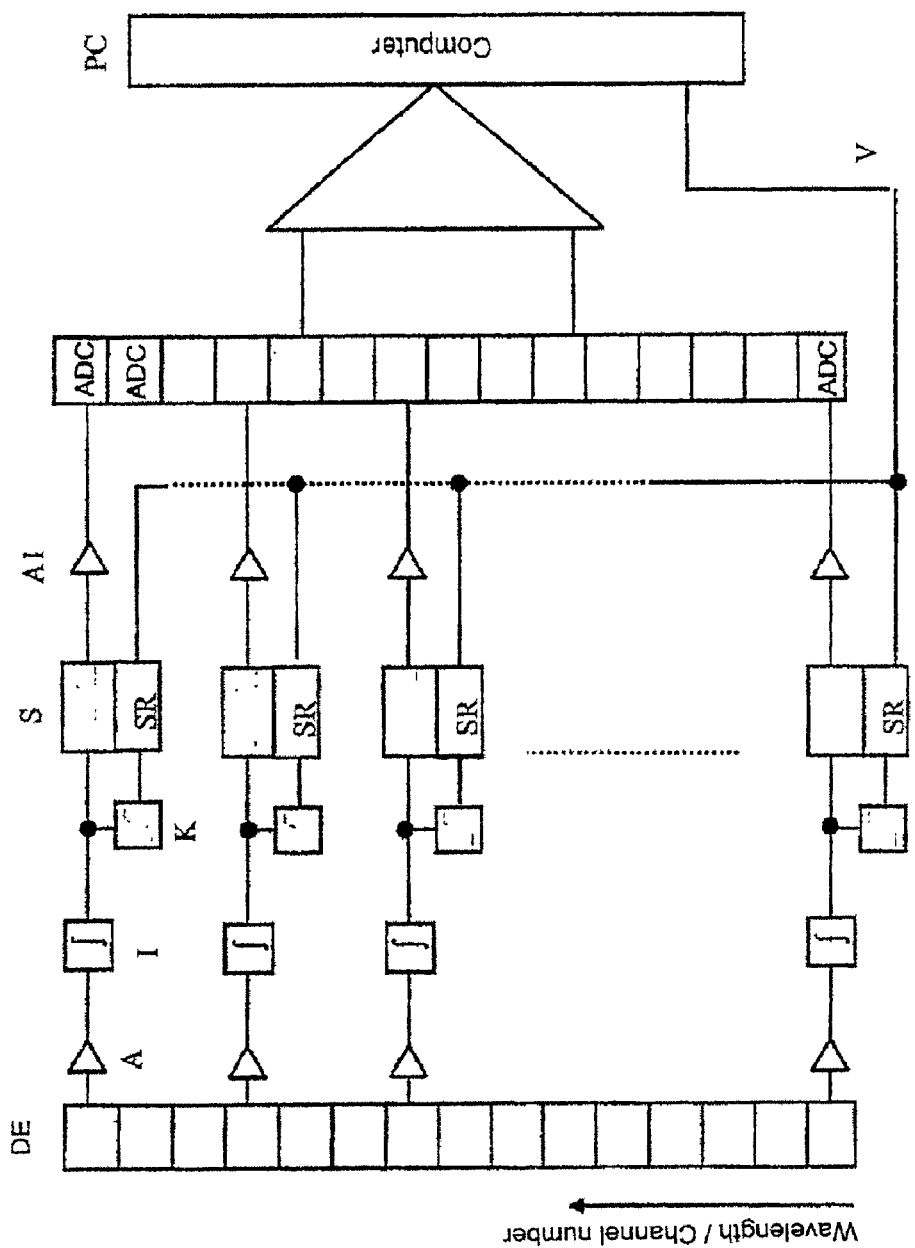
Figure: 7

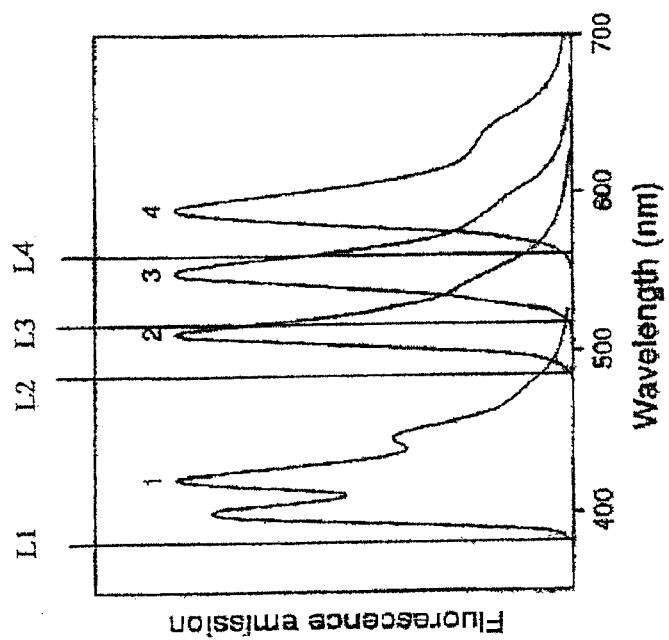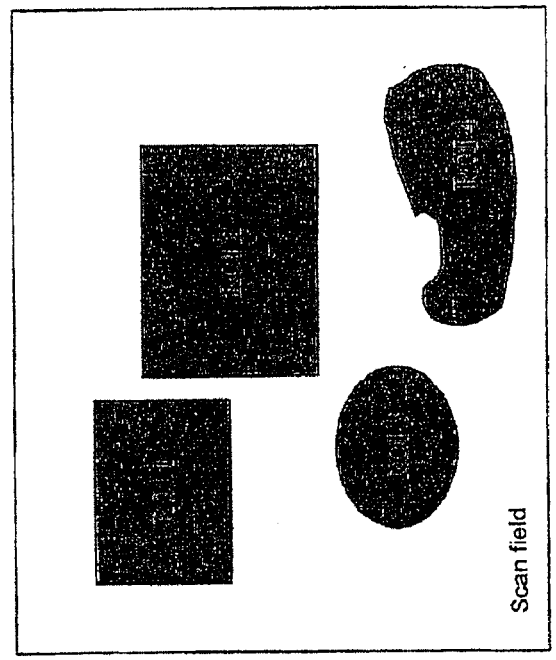
Figure: 8

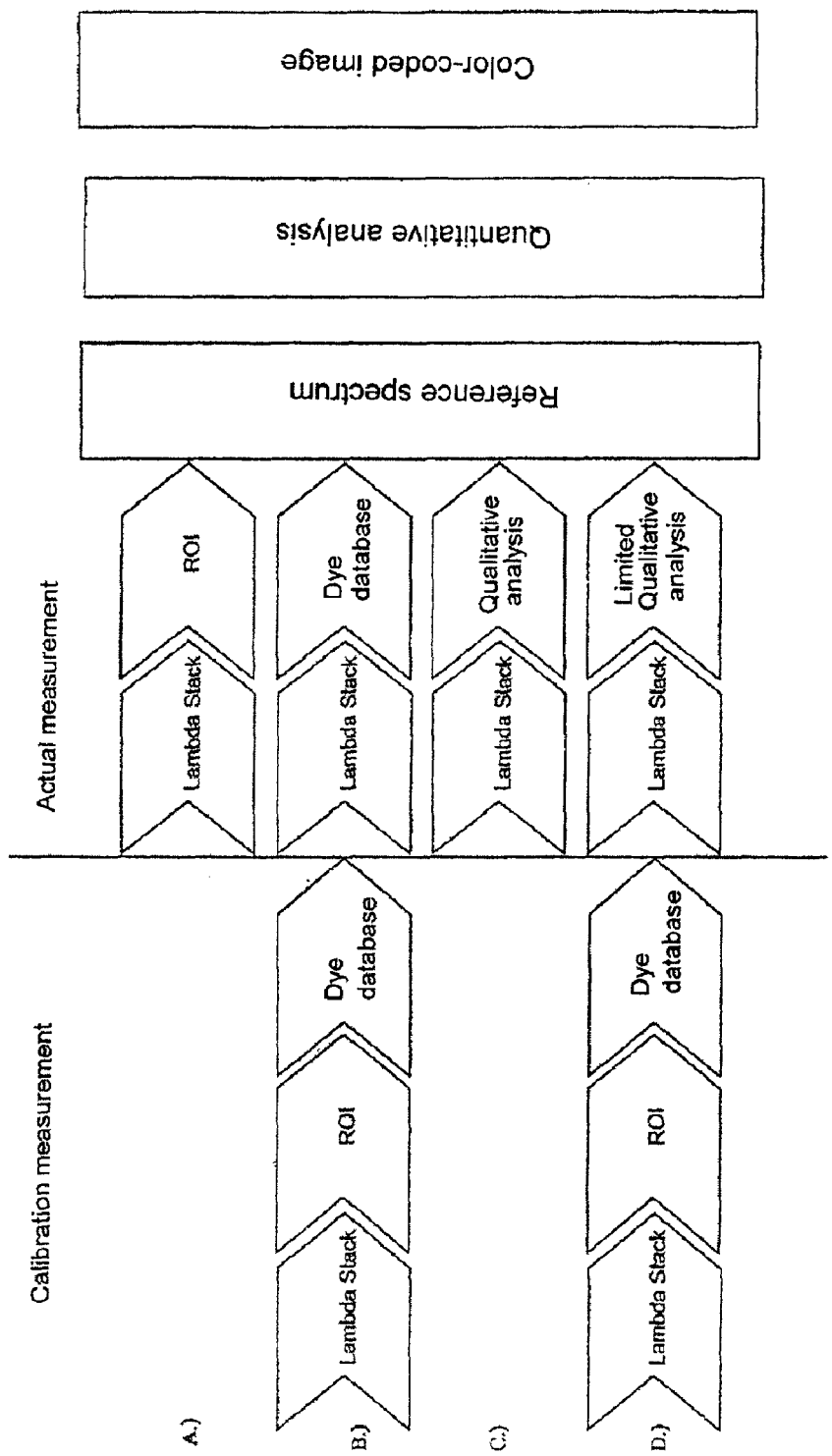
Figure: 9

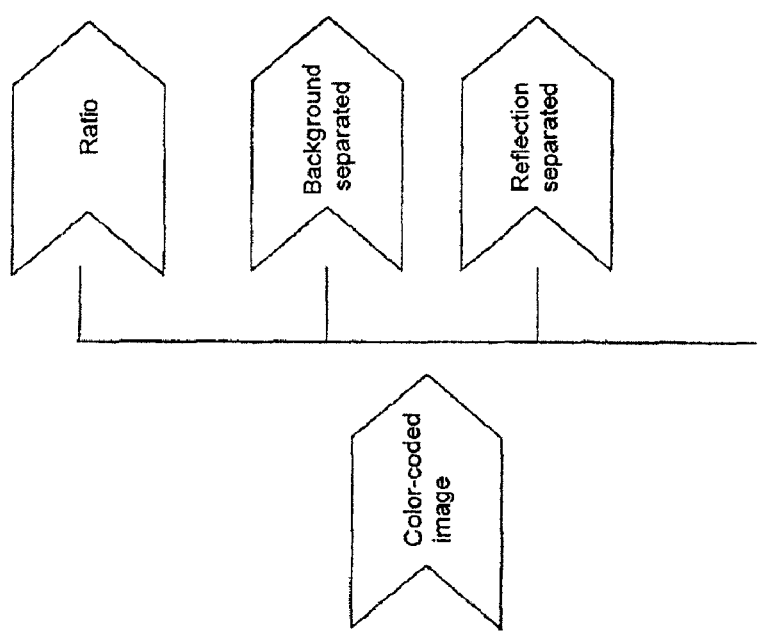
Figure: 10

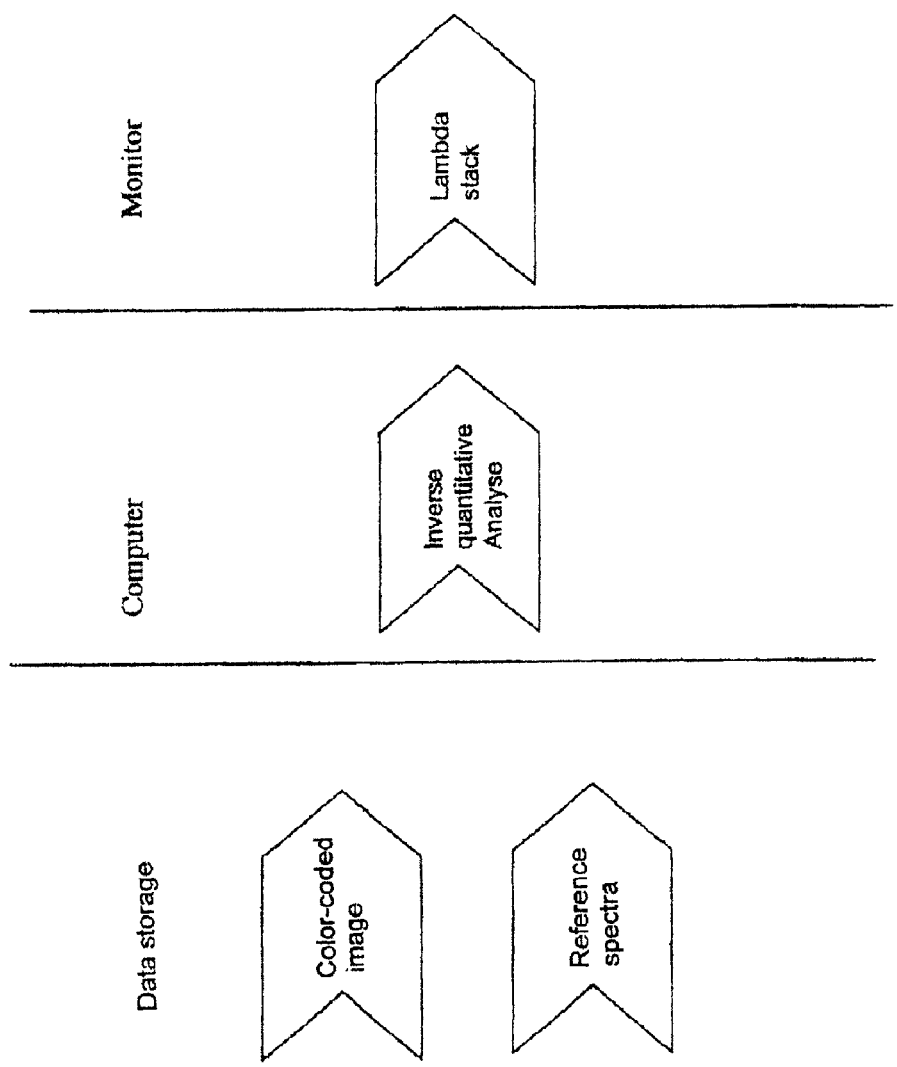
Figure: 11

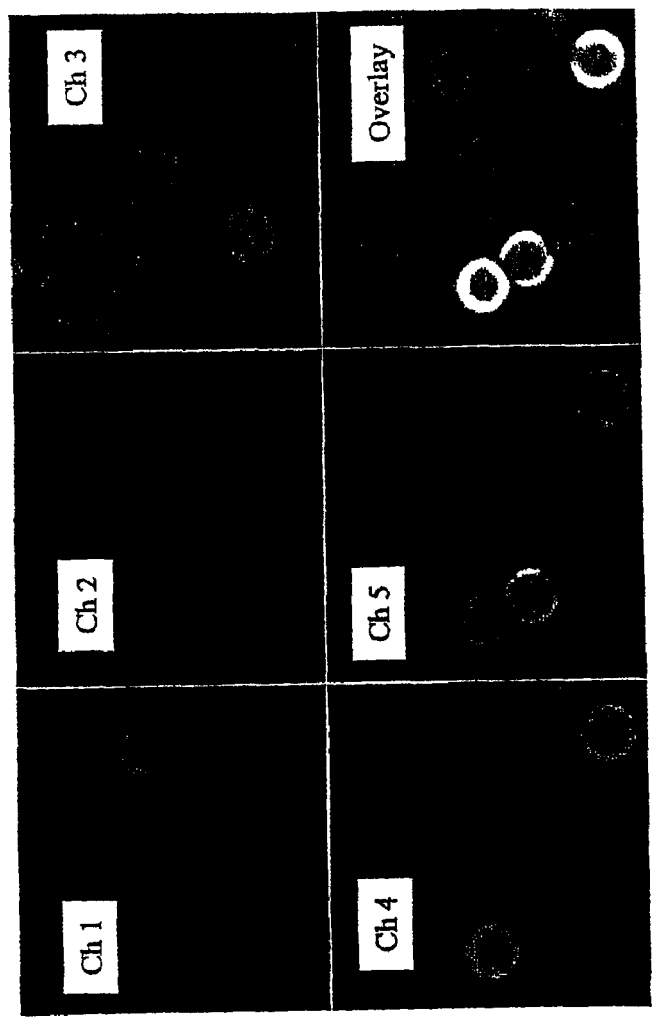
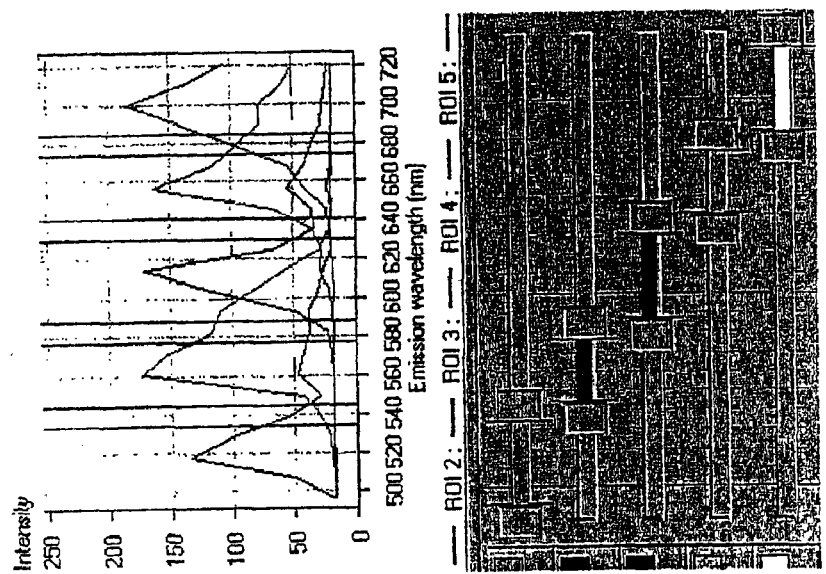
Figure: 12

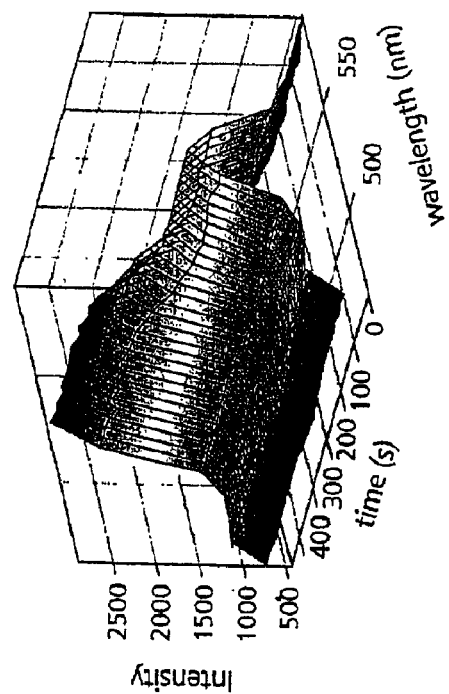
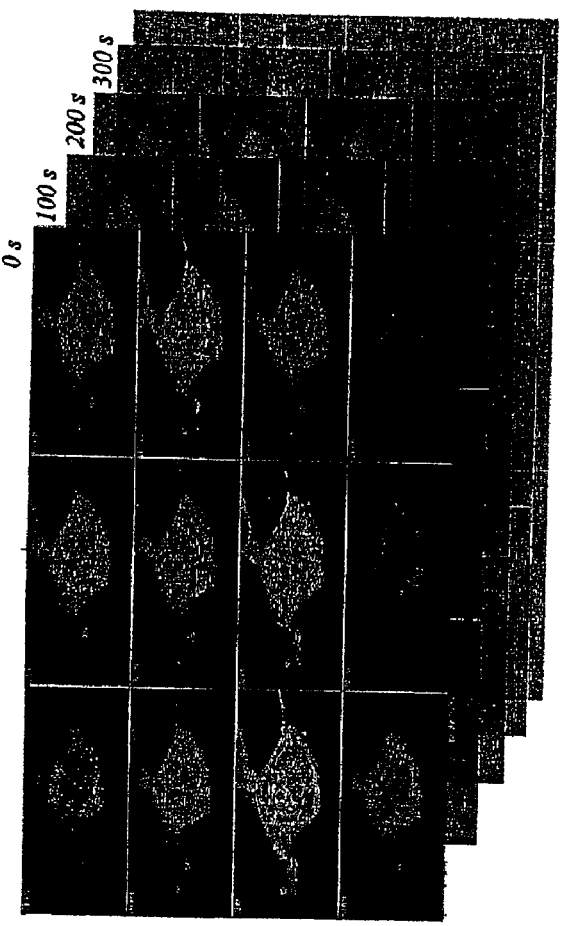
Figure: 13

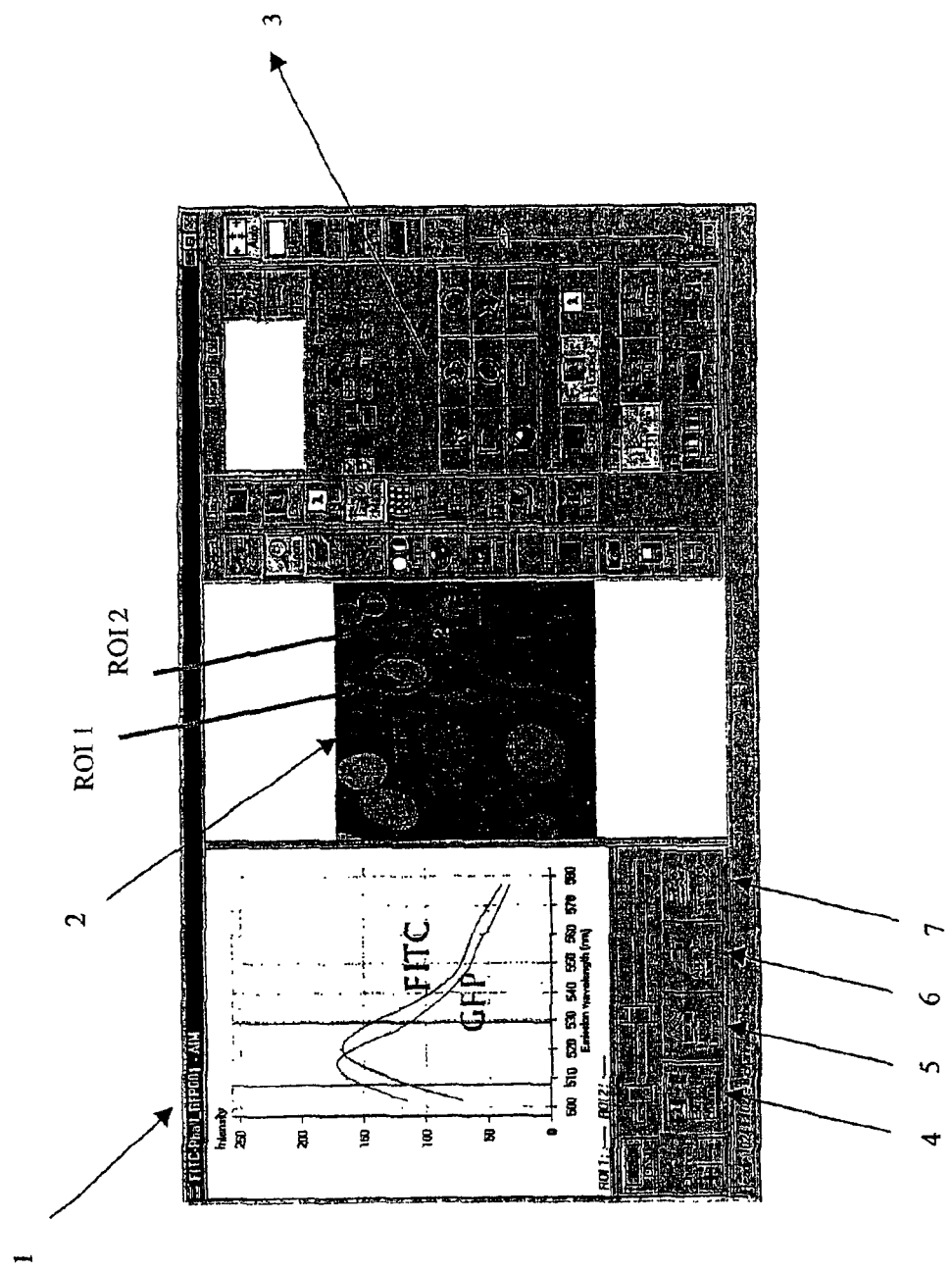
Figure: 14

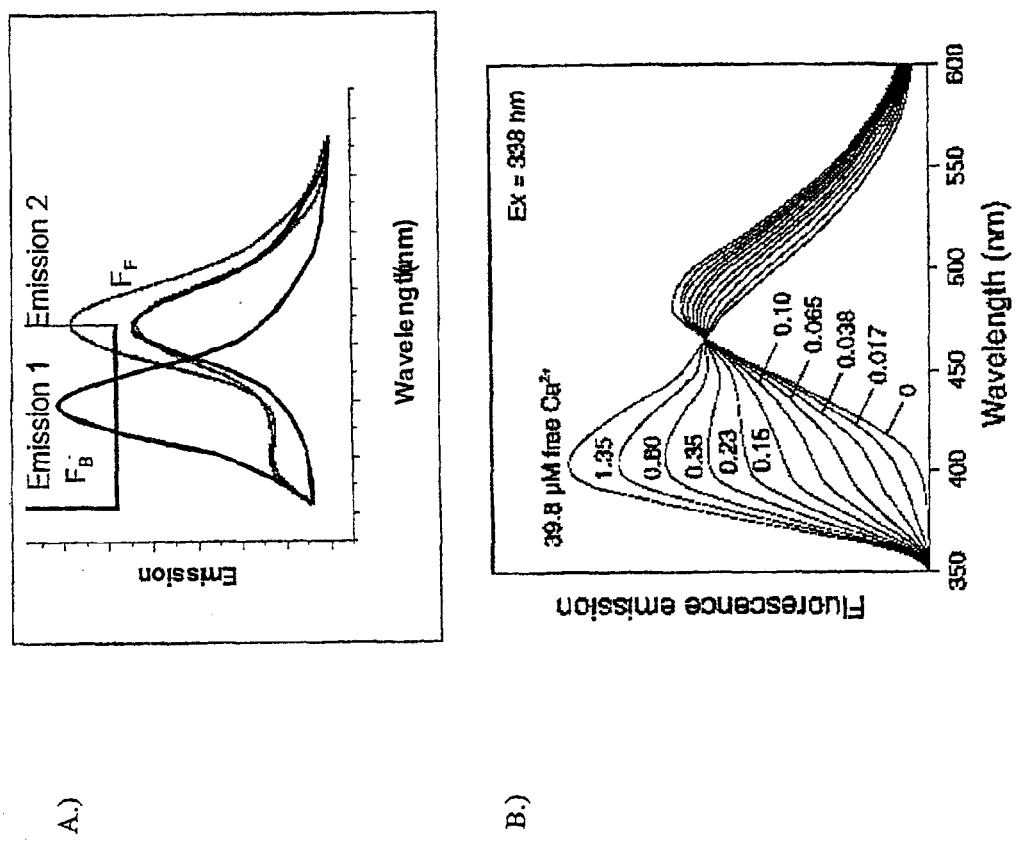
Figure: 15

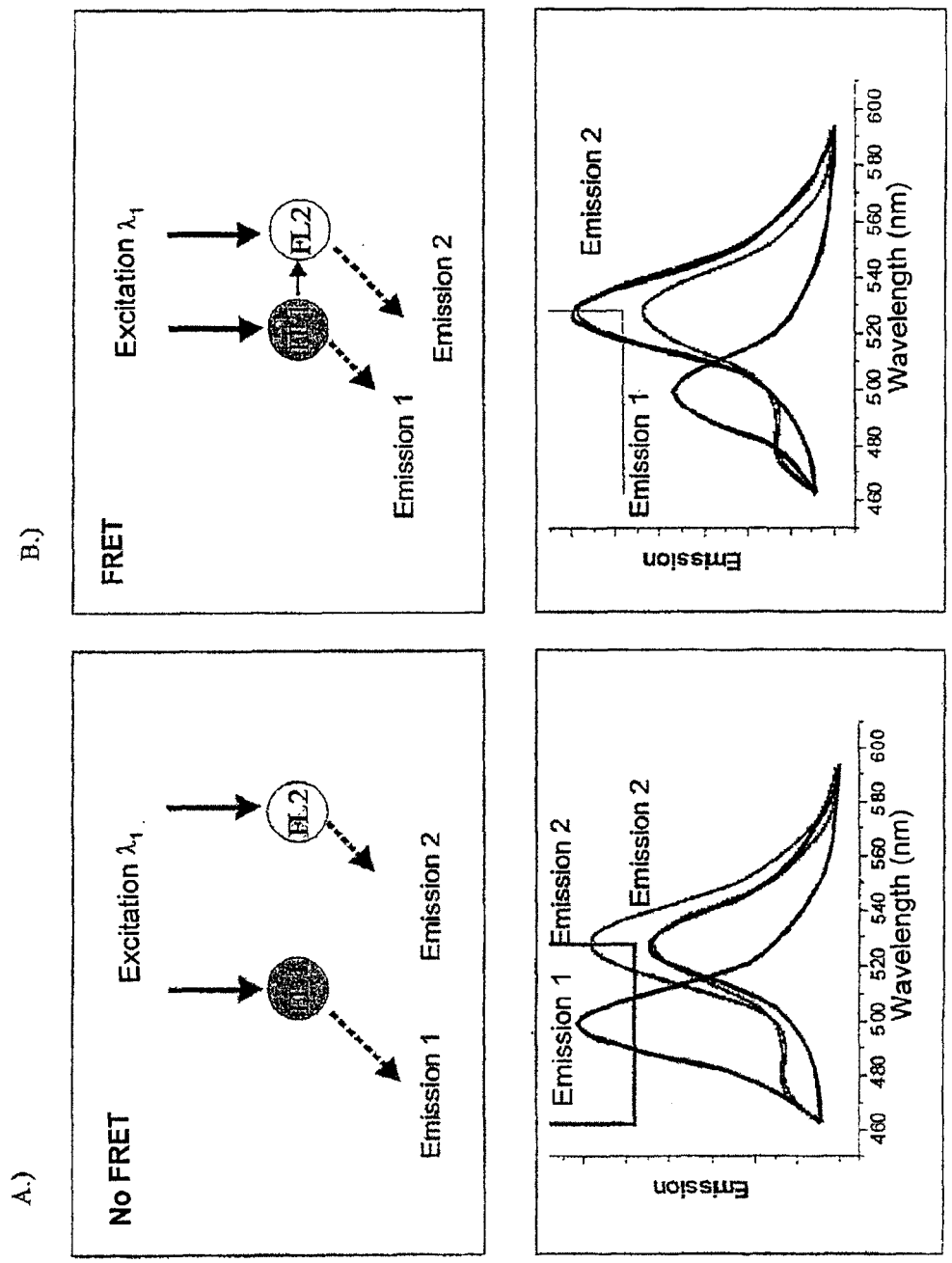
Figure: 16

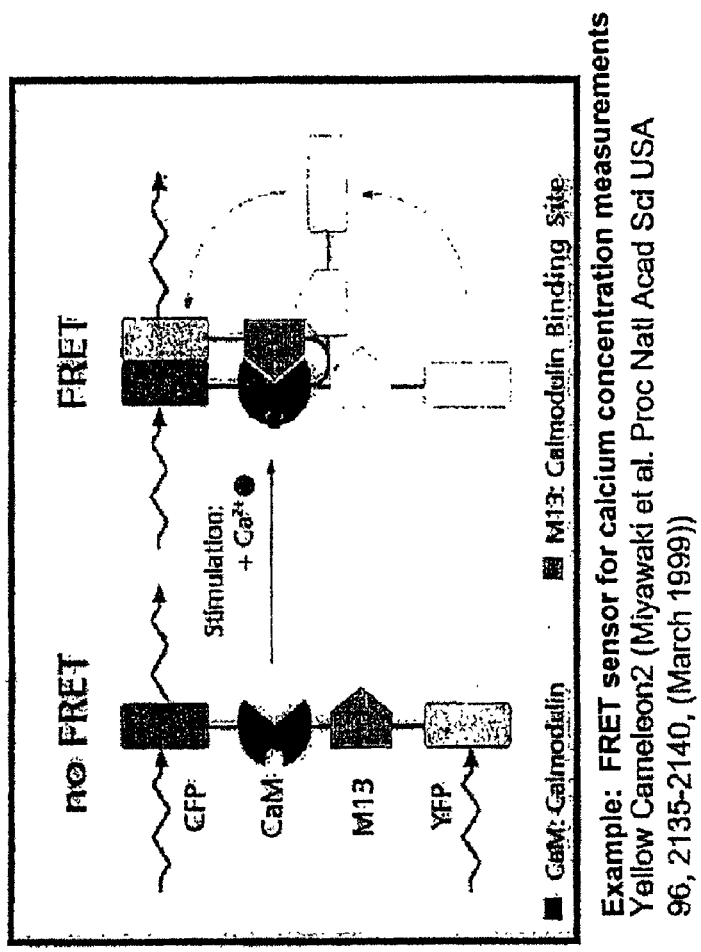
Example: FRET sensor for calcium concentration measurements
Yellow Cameleon2 (Miyawaki et al. Proc Natl Acad Sci USA 96, 2135-2140, (March 1999))
Figure: 17

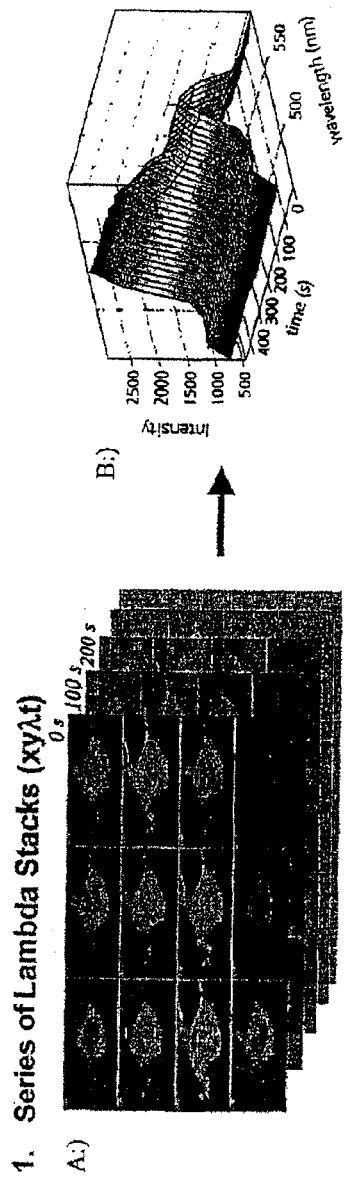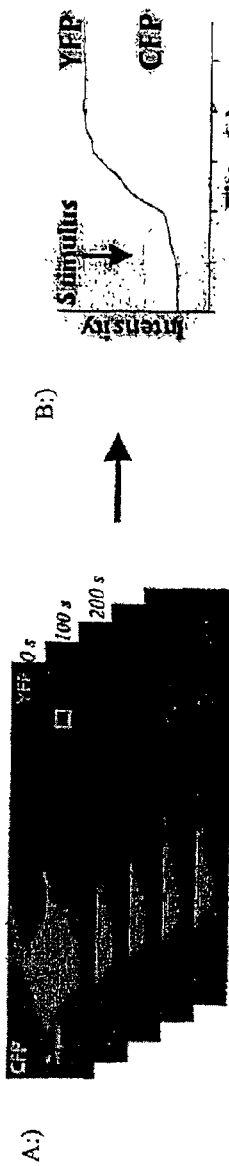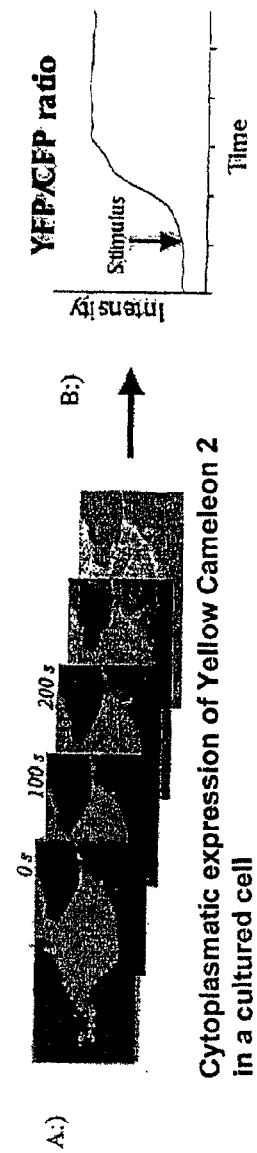
Figure: 18

METHOD FOR INVESTIGATING A SAMPLE

CROSS-REFERENCE TO RELATED APPLICATIONS

This application claims priority of German Application No. 101 51 217.1, filed Oct. 16, 2001, the complete disclosure of which is hereby incorporated by reference.

BACKGROUND OF THE INVENTION a) Field of the Invention

The invention is directed to a method in fluorescence microscopy, particularly laser scanning microscopy, fluorescence correlation spectroscopy, and nearfield scanning microscopy, for the examination of predominantly biological specimens, preparations and associated components. This includes methods for screening active ingredients based on fluorescence detection (high throughput screening). The transition from the detection of a few broad-spectrum dye bands to the simultaneous acquisition of whole spectra opens up new possibilities for the identification, separation and correlation of mostly analytic or functional specimen characteristics to spatial partial structures or dynamic processes. Therefore, simultaneous investigations of specimens with multiple fluorophores are possible with overlapping fluorescence spectra also in three-dimensional structures of thick specimens.

b) Description of the Related Art

A typical area of application of light microscopy for examining biological preparations is fluorescence microscopy (Pawley, "Handbook of Biological Confocal Microscopy"; Plenum Press 1995). In this case, determined dyes are used for specific labeling of cell parts.

The irradiated photons having a determined energy excite the dye molecules, through the absorption of a photon, from the ground state to an excited state. This stimulation or excitation is usually referred to as single-photon absorption (FIG. 1a). The dye molecules excited in this way can return to the ground state in various ways. In fluorescence microscopy, the most important transition is by emission of a fluorescence photon. Because of the Stokes shift, there is generally a red shift in the wavelength of the emitted photon in comparison to the excitation radiation; that is, it has a greater wavelength. Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, multiple parts of a preparation can also be dyed simultaneously with different dyes which bind in a specific manner (multiple fluorescence). Special dichroic beam splitters are used again to distinguish the fluorescence signals emitted by the individual dyes.

In addition to excitation of dye molecules with a high-energy photon (single-photon absorption), excitation with a plurality of lower-energy photons is also possible (FIG. 1b). The sum of energies of the single photons corresponds approximately to a multiple of the high-energy photon. This type of excitation of dyes is known as multiphoton absorption (Corle, Kino, "Confocal Scanning, Optical Microscopy and Related Imaging Systems"; Academic Press 1996). However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

The prior art will be explained more fully in the following by way of example with reference to a confocal laser scanning microscope (LSM) (FIG. 2).

An LSM is essentially composed of four modules: light source, scan module, detection unit and microscope. These modules are described more fully in the following. In addition, reference is had to DE19702753A1.

Lasers with different wavelengths are used in an LSM for specific excitation of different dyes in a preparation. The choice of excitation wavelength is governed by the absorption characteristics of the dyes to be examined. The excitation radiation is generated in the light source module. Various lasers (argon, argon/krypton, Ti:Sa lasers) are used for this purpose. Further, the selection of wavelengths and the adjustment of the intensity of the required excitation wavelength is carried out in the light source module, e.g., using an acousto-optic crystal. The laser radiation subsequently reaches the scan module via a fiber or a suitable mirror arrangement.

The laser radiation generated in the light source is focused in the preparation in a diffraction-limited manner by the objective through the scanner, scan optics and tube lens. The scanner scans the specimen in a point raster in x-y direction. The pixel dwell times when scanning over the specimen are mostly in the range of less than one microsecond to several seconds.

In confocal detection (descanned detection) of fluorescent light, the light emitted from the focal plane (specimen) and from the planes located above and below the latter reaches a dichroic beam splitter (MDB) via the scanner. This dichroic beam splitter separates the fluorescent light from the excitation light. The fluorescent light is subsequently focused on a diaphragm (confocal diaphragm/pinhole) located precisely in a plane conjugate to the focal plane. In this way, fluorescent light components outside of the focus are suppressed. The optical resolution of the microscope can be adjusted by varying the size of the diaphragm. Another dichroic blocking filter (EF) which again suppresses the excitation radiation is located behind the diaphragm. After passing the blocking filter, the fluorescent light is measured by means of a point detector (PMT).

When using multiphoton absorption, the excitation of the dye fluorescence is carried out in a small volume in which the excitation intensity is particularly high. This area is only negligibly larger than the detected area when using a confocal arrangement. Accordingly, a confocal diaphragm can be dispensed with and detection can be carried out directly following the objective (nondescanned detection).

In another arrangement for detecting a dye fluorescence excited by multiphoton absorption, descanned detection is carried out again, but this time the pupil of the objective is imaged in the detection unit (nonconfocal descanned detection).

From a three-dimensionally illuminated image, only the plane (optical section) located in the focal plane of the objective is reproduced by the two detection arrangements in connection with corresponding single-photon absorption or multiphoton absorption. By recording or plotting a plurality of optical sections in the x-y plane at different depths z of the specimen, a three-dimensional image of the specimen can be generated subsequently in computer-assisted manner.

Accordingly, the LSM is suitable for examination of thick preparations. The excitation wavelengths are determined by the utilized dye with its specific absorption characteristics. Dichroic filters adapted to the emission characteristics of the dye ensure that only the fluorescent light emitted by the respective dye will be measured by the point detector.

Currently, in biomedical applications, a number of different cell regions are labeled simultaneously by different dyes (multifluorescence). In the prior art, the individual dyes can be detected separately based on different absorption characteristics or emission characteristics (spectra) (FIG. 3a). FIG. 3a shows the emission spectra of different typical dyes. The emission signal is shown as a function of wavelength. It will be noted that the dyes designated by 1 to 4 differ with respect to the position and shape of their emission spectra. For separate detection, an additional splitting of the fluorescent light of al plurality of dyes is carried out with the secondary beam splitters (DBS) and a separate detection of the individual dye emissions is carried out in various point detectors (PMT x).

The emission spectra of different dyes shown in FIG. 3b can also overlap extensively, so that a separation of the emission signals with DBS is difficult. However, when the dyes have different absorption characteristics, they can be excited selectively by a multitracking method such as that described in DE CZ7302. FIG. 3b shows the emission signals as a function of wavelength for dyes CFP and Cyan-FP in which excitation was carried out with two laser lines at 458 nm and 488 nm. These dyes are particularly suited to examination of living preparations because they have no toxic effect on the specimens to be examined. In order to be able to detect both dyes CFP, CFT as efficiently as possible, CFP is excited with a wavelength of 458 nm in one scanning direction and detected with fluorescence of 460–550 nm. The selective excitation of GFP with 488 nm and the detection of the wavelength range of 490–650 nm is carried out on the return path of the scanner.

When the position of the emission spectrum of the utilized dyes is unknown or when a shift occurs in the emission spectrum depending on environment (inside and outside the specimen: temperature, concentration, pH) (FIG. 3c), efficient detection of the dye fluorescence is possible only conditionally. FIG. 3c again shows the emission signal as a function of wavelength. The wavelength shift can amount to about 10 nm. Spectrometers are also currently used in combination with an LSM to measure the emission spectrum in the specimen. In so doing, a conventional, usually high-resolution spectrometer is used instead of a point detector (Patent: Dixon, et al. U.S. Pat. No. 5,192,980). However, these spectrometers can record an emission spectrum only point by point or as an average over a region. Accordingly, this is a kind of spectroscopy.

In another application of fluorescence microscopy, the ion concentration (e.g., Ca+, K+, $Mg^{2+}$, $ZN^+$, . . . ) is determined, particularly in biological preparations. Special dyes or dye combinations (e.g., Fura, Indo, Fluo; Molecular Probes, Inc.) having a spectral shift depending on the ion concentration are used for this purpose. FIG. 4a shows the emission spectra of Indo-1 as a function of the concentration of calcium ions. FIG. 4b shows an example of the emission spectra depending on the calcium ion concentration using the combination of Fluo-3 and Fura Red dyes. These special dyes are known as emission ratio dyes. When the two fluorescence regions shown in FIG. 4a are summed and the ratio of both intensities is taken, the corresponding ion concentration can be determined. In these measurements, the examination is usually directed to dynamic change in the ion concentration in living preparations requiring a time resolution of less than one millisecond.

Superimposition of background signals is a troublesome, unwanted effect in multifluorescence recordings. These background signals can be reflections of individual lasers on the specimen or broadband autofluorescence signals of specimen components which are superimposed on the spectral signatures of the fluorescence-labeled specimen locations to be investigated and therefore render this investigation more difficult or sometimes even impossible.

Flow cytometers are used for investigating and classifying cells and other particles. For this purpose, the cells are dissolved in a liquid and are pumped through a capillary. In order to examine the cells, a laser beam is focused in the capillary from the side. The cells are dyed with different dyes or fluorescing biomolecules. The excited fluorescent light and the backscattered excitation light are measured. The art is described in "Flow Cytometry and Sorting", second edition, M. R. Melamed, T. Lindmo, M. L. Mendelsohn, eds., Wiley & Sons, Inc., New York, 1990, 81–107.

The size of the cells can be determined from the backscattered signal. Different cells can be separated and/or sorted or counted separately by means of the spectral characteristics of the fluorescence of individual cells. The sorting of the cells is carried out with an electrostatic field in different capillaries. The results, that is, for example, the quantity of cells with dye A in comparison to cells with dye B, are often displayed in histograms.

The through-flow rate is typically about 10–100 cm/s. Therefore, a highly sensitive detection is necessary. According to the prior art, a confocal detection is carried out in order to limit the detection volume.

The accuracy of the through-flow measurement is influenced by different factors. Such factors are, for example, nonspecific fluorescence, autofluorescence of cells, fluorescence of optical components and the noise of the detectors.

OBJECT AND SUMMARY OF THE INVENTION

The invention has as its primary object novel methods for flexible and freely programmable detection by which dyes which differ from each other only slightly with respect to their absorption characteristics and emission characteristics can be measured and displayed separately in an image-generating microscope system. With the method according to the invention, crosstalk between the individual dyes is reliably detected and eliminated by data processing.

In accordance with the invention, a method for investigating specimens, wherein a spectral splitting of the radiation coming from the specimen is carried out for specimen points or point distributions, for the operation of a laser scanning microscope or a fluorescence screening arrangement or a flow cylinder comprising the steps of generating a λ-stack so that the spectral distribution is measured by individual detection channels and storing the signals so as to be correlated to the detection signals with at least one of the spatial coordinates x, y and z and/or so as to be correlated to the measurement time t.

These methods can be used in image-generating and analytic microscope systems. The microscope systems are image-generating systems such as laser scanning microscopes for three-dimensional examination of biological preparations with an optical spatial resolution of up to 200 nm, nearfield scanning microscopes for high-resolution examination of surfaces with a resolution of up to 10 nm, fluorescence correlation microscopes for quantitative determination of molecular concentrations and for measuring molecular diffusions. Also included are methods based on fluorescence detection for screening dyes and methods for flow cytometry.

In all of the systems mentioned above, fluorescent dyes are used for specific labeling of the preparations.

The quantity of dye signatures that may be used simultaneously, i.e., the quantity of characteristics, for example, of cells that can be investigated simultaneously, can be increased by means of the method according to the invention. When the spectral signatures of the individual dyes overlap extensively, the wavelength range must be limited, according to the prior art, for separate detection of the fluorescence signals of individual dyes. This reduces the sensitivity of detection, i.e., increases the noise of the detectors, because greater amplification is used. This is avoided by the method according to the invention. Further, nonspecific fluorescence signals, autofluorescence and fluorescence of the measuring device can be separated out.

BRIEF DESCRIPTION OF THE DRAWINGS

In the drawings:

FIG. 1a is a representational view of single photon absorption;

FIG. 1b is a representational view of a excitation with a plurality of lower-energy photons;

FIG. 2 is a block schematic view of a confocal laser scanning microscope;

FIG. 3a is a graphical representation of emission spectra of different typical dyes;

FIG. 3b is a graphical representation of emission signals as a function of wavelength for dyes CFP and Cyan-FP in which excitation was carried out;

FIG. 3c is a graphical representation of the emission spectrum of utilized dyes showing a wavelength shift;

FIG. 4a is a graphical representation showing the sum of two fluorescence regions and the ratios of both intensities is taken;

FIG. 4b is a graphical representation showing an example of the emission spectra depending on the calcium ion concentration using the combination of Fluo-3 and Fura Red dyes;

FIG. 5 illustrates a block diagram of the detector unit in accordance with the invention;

FIG. 6 shows a possible embodiment form of the optical beam path of the detector unit shown in the block diagram in FIG. 5;

FIG. 7 schematically shows an arrangement for reading out the individual channels of the detector in accordance with the invention;

FIG. 8a schematically shows a distribution of ROIs in an LSM image which represent, for example, different regions of a cell;

FIG. 8b illustrates associates typical emission spectra with associated wavelengths;

FIG. 9(a–d) show in representational fashion how reference spectra can be used for calculating the contribution of the dye states to the fluorescence emission in the image points of a lambda stack or a series of lambda stacks;

FIG. 10 shows in representational form division of signals classified in two different image channels;

FIG. 11 shows in representational form how quantitatively analyzed data records and the reference spectra are stored, on a data medium;

FIG. 12a shows in graphical form how wavelength regions can be selected by the spectral signatures and the intensity values of the corresponding planes of the lambda stack can be continued;

FIG. 12b shows in pictorial form the multichannel image that can be generated from the FIG. 12 approach;

FIGS. 13a and 13b show in pictorial form different displays when lambda stacks are acquired over time;

FIG. 14 shows in pictorial form how the RO1 function can be used to make visible the spectral signatures of any selected specimen locations;

FIG. 15a shows in graphical form two states of the dye contribute to the emission spectrum measured at a given time in the observational volume;

FIG. 15b shows in graphical form that the emission spectra associated with the bonding states in vivo and in vitro are determined by this arrangement and by the ROIs to be determined by the user;

FIGS. 16a and 16b show in representational and graphical form the emission spectrum for the FRET partners for different distances between the donor and acceptor (A-great distance, no FRET, B-small distance, FRET interaction;

FIG. 17 shows in pictorial form an example of a FRET sensor for calcium concentration measurements;

FIGS. 18 1)a and 18 1)b show a graphical result (intensity versus time versus wavelength) for a series of lambda stacks;

FIGS. 18 2)a and 18 2)b show a graphical result (intensity versus. time) for a series of images with CFP and YFP signals after linear unmixing analysis; and FIGS. 18 3)a and 18 3)b show a series of ratio images (intensity versus time) (YFP/CFP).

DESCRIPTION OF THE PREFERRED EMBODIMENTS

The background of the method according to the invention is a spectrally split detection of fluorescence. For this purpose, the emission light is split from the excitation light in the scan module or in the microscope (with multiphoton absorption) by means of an element for separating the excitation radiation from the detected radiation, such as the main color splitter (MDB) or an AOTF according to 7346DE or 7323DE. With transmitted-light arrangements, this type of element can also be entirely omitted. A block diagram of the detector unit to be described is shown in FIG. 5. With confocal detection, the light L from the specimen is focused through a diaphragm (pinhole) PH by means of imaging optics PO, so that fluorescence occurring outside of the focus is suppressed. In nondescanned detection, the diaphragm is omitted. The light is now divided into its spectral components by an angle-dispersive element DI. The angle-dispersive elements can be prisms, gratings and, e.g., acousto-optic elements. The light which is split into its spectral components by the dispersive element is subsequently imaged on a line detector DE. This line detector DE measures the emission signal as a function of wavelength and converts it into electrical signals ES. In addition, a line filter for suppressing the excitation wavelengths can be arranged in front of the detection unit.

FIG. 6 shows a possible embodiment form of the optical beam path of the detector unit shown in the block diagram in FIG. 5. The construction is essentially a Czerny Turner construction. In confocal detection, the light L of the specimen is focused through the confocal diaphragm PH by the pinhole optics PO. With nondescanned detection in case of multiphoton absorption, this diaphragm can be omitted. The first imaging mirror S2 collimates the fluorescent light. Subsequently, the light strikes a line grating G, for example, a grating with a line number of 651 lines per mm. The grating bends the light in different directions corresponding to its wavelength. The second imaging mirror S1 focuses the individual spectrally split wavelength components on the corresponding channels of the line detector DE. The use of a secondary electron multiplier array by Hamamatsu H7260 is especially advantageous. The detector has 32 channels and high sensitivity. The free spectral region of the embodiment form described above is approximately 350 nm. In this arrangement, the free spectral region is uniformly distributed to the 32 channels of the line detector resulting in an optical resolution of approximately 10 nm. Therefore, this arrangement is suitable for spectroscopy only conditionally. However, its use in an image-generating system is advantageous because the signal per detection channel is still relatively large due to the relatively broad detected spectral band. A shift of the free spectral region can be carried out in addition, for example, by rotating the grating by DP.

In the embodiment form(s) described above, each individual channel of the detector DE detects a spectral band of the emission spectrum with a spectral width of approximately 10 nm. The sum of the spectral components of the individual dyes at the image point that has just been measured is recorded for each image point. In addition, the user can switch off any individual channels by means of the switch register SR which will be described in the following. This is particularly useful for suppressing one or more excitation laser lines.

An arrangement for reading out the individual channels of the detector DE is shown schematically in FIG. 7. In this case, the current at the anode of a multichannel PMT is converted to voltage and amplified through the first amplifier A (connected as current-voltage converter). The voltage is fed to an integrator I which integrates the signal over a corresponding time period (e.g., pixel dwell time).

For faster evaluation, the integrator I can be followed by a comparator K which, as a simple comparator, has a switching threshold such that a digital output signal is generated when this threshold is exceeded or which is constructed as a window comparator and then forms a digital output signal when the input signal lies between the upper and lower switching threshold or when the input signal lies outside (below or above) the switching thresholds. The comparator or window comparator can be arranged before as well as after,the integrator. Circuit arrangements without an integrator (so-called amplifier mode) are also possible. With the amplifier mode arrangement, the comparator K is also present after corresponding level matching. The output of the comparator K serves as a control signal for a switch register SR which directly switches the active channels (on-line), or the state is conveyed to the computer via an additional connection V in order to make an individual selection of active channels (off-line). The output signal of the switch register SR is fed directly to another amplifier A1 for level matching for the subsequent analog-to-digital conversion AD. The A-D-converted values, i.e., the spectrally resolved fluorescence signal of the specimen, are transferred via a suitable data line to a computer (PC or digital signal processor DSP) for data processing. Subsequently, depending on the scan mode, lambda stacks (spectral distribution per image point, measured by the detection channels with dispersive splitting of detected radiation stored in storage elements with allocation to at least one additional (image point) coordinate x, y and/or Z and/or measurement time t) are formed from the individual image points that are measured in a spectrally resolved manner with the additional coordinates x, y, z, time and lifetime, where X and Y are scanned by SC;

Z is carried out, for example, by displacing the preparation along the optical axis;

Time: the data acquisition is carried out at different times;

Lifetime: the data acquisition is carried out:in a time-resolved manner within the fluorescence lifetime.

In fluorescence measurement, it is useful for prevention of artifacts to suppress the excitation light backscattered from the specimen or at least to reduce it to the extent that it is less than, or on the same order of magnitude as the emission maximum. For this purpose, the additional line filter, described above, or a correspondingly optimized main color filter (MDB) can be used for optical attenuation. Since the spectral width of the excitation laser radiation is very much smaller than the bandwidth detected by the individual channel, the backscattered or reflected excitation radiation can also be effected by deliberately switching off the corresponding channel with the SR shown in FIG. 7. When the excitation wavelength strikes two detection channels, the excitation line can be shifted by means of a rotation of the grating, a displacement of the line detector or a tilting of S1 or S2 in FIG. 6 in such a way that it only strikes one detection channel.

In the arrangements described above, an integrator circuit was preferably used for detecting the individual channel signals However, a photon count can also take place in the individual channels and the photon numbers can be added, without any limitation.

Various methods for displaying the information of the specimen, i.e., the lambda stacks, are described in the following.

In its simplest form, a lambda stack acquired by the method described above is a stack of x-y images which contain the fluorescence intensity values from adjacent, very narrow wavelength regions. More complex data are obtained by combining the acquisition of this lambda stack with z-stacks and/or time series.

These data can be prepared for the observer in different ways:

a) Lambda maximum projection

In this case, a gray scale image is generated: from the lambda stack in that the maximum intensity value which defines the brightness of the corresponding pixel of the projection image is determined for every x-y pixel position over the wavelength regions.

b) Lambda coded projection

In this case, as in a), a lambda maximum projection is calculated and every pixel is provided with the color which corresponds to the mean wavelength of the wavelength region from which the brightest pixel of the lambda stack originates.

c) Gallery view for a simple lambda stack (xyλ)

In this case, the individual images of the lambda stack are displayed at least partially in a series. For this purpose, the mean wavelength of the region in which the intensities were recorded can be indicated for every image.

d) Gallery view for more complex lambda stacks

When xy-lambda stacks are acquired over z and/or over time, slides can be used in order to allow the respective series of a z-plane or time point to be shown in the gallery. In another way, all acquired xy-images can be displayed simultaneously in that the images differing in spectra are shown in lines and the images differing with respect to time or in the z-plane are shown in columns. The following gallery views can be selected: xy-λ, xy-z, xy-t, xy-λ-z, xy-λ-t, xy-z-t. The dimensions not mentioned can be scrolled through by means of slides.

Simultaneous display of xy-z-t-λ information is made possible by combining the lambda max projection or lambda coded projection with the gallery view in lines and columns.
e) Orthogonal sections though lambda stacks This display shows a selected λ-plane of a lambda stack with a horizontal marking line and a vertical marking line which can be positioned freely. The lambda stack is sectioned at these lines and the resulting section image adjacent to (y-section) and along (x-section) the λ-plane is projected. A pseudo true-color coding can be carried out optionally. In so doing, each wavelength region is assigned its corresponding spectral color. A true-color imaging of the specimen results by superimposing the individual color components in an image.

Reference spectra are, e.g., the emission spectra of individual dyes in their purest form, i.e., dissolved in solvent or bonded in individual discrete regions of the specimen to be investigated. The selection of the regions for generating the reference spectra can be carried out by the following methods.

Lambda stacks contain the spectral information for each pixel, in addition. FIG. 8a schematically shows a distribution of different ROIs (ROI 1–4) in an LSM image which represent, e.g., different colored regions of a cell. Typical associated emission spectra 1–4 are shown with their excitation wavelengths (L1–L4) in FIG. 8b. The user can adjust the ROIs as follows, for example: After a lambda stack is recorded using all or most of the excitation lines needed for exciting a lambda stack in the individual ROIs, sum channels can be formed between the individual excitation lines (L1 to L2, L2 to L3, L3 to L4 and L4, according to FIG. 8b, up to the maximum emission wavelength). These sum channels correspond to parts of the fluorescence bands of the individual dyes. Further, a simultaneous summation of the signals of different dyes is carried out in the same sum channels because of the extensive overlapping. These sum channels are subsequently stored in different image channels in a color-coded manner and are shown or superimposed on one another. Because of the different local color mixing:in the image channels, the different ROIs can be located by the user or by automatic pattern recognition.

In a second method for adjusting the different ROIs, the fluorescence centroid CZ 7447 is measured. For this purpose, all individual channels that are irradiated with excitation laser lines are switched off in the detector. Every ROI has a characteristic fluorescence centroid because of the changed emission characteristics of the dyes. The different ROIs can accordingly be distinguished by the position of the characteristic color centroid and made visible separately.

The user can use the ROI function (ROI=Region Of Interest; see FIG. 14) to make visible the spectral signatures of any selected specimen locations. In so doing, an area (ROI 1 and ROI 2 in FIG. 14) of an acquired specimen is marked in image 2 with a tracing tool 3 (e.g., polygon, ellipse or closed spline) and the graph of the corresponding spectral signature is determined graphically (diagram 1) by averaging the x-y pixels enclosed in the ROI for every λ-plane of the lambda stack.

In principle, a plurality of spectral signatures of different selected specimen locations can be displayed simultaneously either in a common diagram 1 or in separate diagrams 1.

The visualized spectral signatures 1 give information about the spectral distribution of the fluorescence emission in the selected specimen locations. When a plurality of spectral signatures of different ROIs are displayed, it can be determined, for example, whether the emission spectra of the dyes overlap significantly.

As is shown in FIG. 12, the spectral signatures of the different ROIs can be used to generate a color-coded multichannel image ("extract to channels" operating control, FIG. 14 (4)). Wavelength regions can be selected (FIG. 12a: ROI 1 to 5) by means of the spectral signatures and the intensity values of the corresponding planes of the lambda stack can be combined, e.g., by summation or averaging over the corresponding wavelength regions for every image point, in order to generate a multichannel image (FIG. 12b), wherein every image channel represents a dye (Ch 1 to CH 5).

In addition, this adjustment can be used for electronic summation (see FIG. 7) of the individual channels ("extract to hardware", FIG. 14 (6)). Subsequently, multichannel images can be directly scanned with the corresponding adjustments.

The spectral signatures of individual ROIs, i.e., individual dyes in their specific environment, can be stored in a spectral database (FIG. 14 (7)) for subsequent reuse; in addition to the data of the graphs, the specific parameters for the recording of the lambda stack, such as the laser lines, intensities, filter configurations (MDB, NFT, EF) and adjustment of the detector (amplification, integration time, pinhole position and pinhole diameter) and additional comments on the environment and/or preparation of the preparation to be investigated can also be stored.

When the lambda stack is acquired over a time period, spectral signatures can be determined at different times and combined in a series. Subsequently, these data can be visualized in a three-dimensional display, e.g., corresponding to FIG. 13b, and the change in the spectral signatures over time in different ROIs can be conveyed. In an advantageous manner, this display can be used with two or more fluorescence dyes simultaneously during the evaluation of experiments such as FRET (Fluorescence Resonance Energy Transfer) or FRAP (Fluorescence Recovery After Photobleaching) (see FIG. 13). Drawing part b shows the fluorescence signal (intensity) as a function of wavelength and time. It will be seen that the signal in the wavelength range of 530 nm to 560 nm increases with time. Another display is shown in FIG. 13a. The spectral individual channels are shown at different points in time. Every drawing part represents a wavelength range of 10 nm, for example.

Algorithms for analysis, e.g., for selective display of the contributors of individual dyes to the total fluorescence signal radiated from the specimen are described in the following. The analysis can be carried out quantitatively or qualitatively. In a quantitative analysis, the contribution (i.e., concentration) of every individual dye to the total fluorescence signal radiated from the specimen is calculated for every image point. Algorithms such as, e.g., linear unmixing analysis (Lansford, et al., Journal of Biomedical Optics 6(3), 311–318, (July 2001)) are used. Reference spectra, as they are called, are needed for the analysis. These reference spectra describe the fluorescence spectrum of an individual dye. The accuracy of the results depends decisively on the accuracy of the reference spectra. Therefore, in a method according to the invention, the reference spectra are acquired simultaneously during the investigation of the preparation (see below). The contributions of the respective dyes are ordered in different image channels and a specific color is allocated to every image channel. The brightness of the color is determined by the size of the contribution. Subsequently, the individual image channels can be displayed superimposed in an image and a color-coded (lambda-coded) image results.

In qualitative analysis, a classification is carried out, i.e., only the dye generating the greatest contribution to the total fluorescence signal radiated by the specimen is allocated to every image point. The allocation is carried out again in an image in different image channels and a specific color can be allocated to every image channel. Algorithms such as a principal component analysis (PCA, I.T. Joliffe, *Principal Component Analysis*, Springer-Verlag, New York, 1986) are used for this purpose. Through this type of algorithm, a masking of the image (dye mask) is obtained, wherein identical dyes are located in regions of the same color.

Method steps for separating dye fluorescences will be described in the following.

When the spectral signatures of the selected ROIs represent only the emission signal of exactly one of the utilized dyes in the specimen (reference spectra), they can be used in a particularly advantageous manner for a quantitative analysis (e.g., digital unmixing, FIG. 14 (5)) of the emission signals (FIG. 9a). The input data of this quantitative analysis are a lambda stack, upon which the analysis is based, and the spectral signatures of n selected specimen locations (ROI), where n is the quantity of dyes used in the sample. The result of the quantitative analysis (e.g., unmixing) is an image comprising n individual image channels, each of which contains only the information of the emission signals of one dye.

Another procedure for quantitative analysis (e.g., digital unmixing) of the emission signals uses, as input data, a lambda stack and reference spectra for the latter which have been stored beforehand in a spectrum database (FIG. 9b). These reference spectra can come from an experiment (calibrating measurement) in which a specimen (or specific regions) was marked with only exactly one fluorescence dye. This procedure is required, for example, when the dyes are predominantly colocalized in the actual experiment and, accordingly, a specimen location with a pure emission signal without spectral crosstalk of another emission can not found for every dye, i.e., no ROI can be marked.

In addition, the reference spectra from the database can be selected by the user before the lambda stack is acquired and a quantitative analysis (e.g., digital unmixing) of the lambda stack can be carried out immediately during acquisition. As a result, the image of n-channels is displayed on the screen. A memory-intensive buffer storage of the lambda stack data can be dispensed with in this case.

In another method which is shown schematically in FIG. 11, quantitatively analyzed data records (color-coded image) and the reference spectra are stored, in accordance with the quantity of dyes, on a data medium instead of the lambda stack. This has the advantage that the size of the data record can be stored without a serious loss of signal information. For example, when a lambda stack with 32 individual channels in 512×512 image points and 8 bits is detected, the size of the image stack is approximately 16 megabytes. By storing the color-coded image, the size of the data record is reduced by a factor of 32 to approximately 0.5 megabytes, not including the reference spectra. The quantity of data points in the reference spectra is 32 multiplied by the quantity of dyes. The lambda stack can be calculated again subsequently in the computer from the stored data (reference spectra) and color-coded image. In the simplest case, the calculation is carried out by multiplying the reference spectra by the respective image channels of the colorcoded image. Data reduction is necessary particularly when so-called time series or time series with three-dimensional image information are recorded.

In another method whose flow chart is shown in FIG. 9c, a qualitative analysis is carried out in the first step starting from the lambda stack. On the one hand, areas in the preparation in which identical dyes are spatially distributed can be found through this analysis. On the other hand, the reference spectra required for the subsequent quantitative analysis can be generated automatically without user intervention. Apart from the lambda stack, no additional input parameters are needed for the qualitative analysis, e.g., PCA. The reference spectra obtained in this way and the lambda stack are then used as input parameters for a quantitative analysis, which again results in a color-coded image.

In another method according to FIG. 9D, a limited qualitative analysis of the lambda stack is carried out. In the limited qualitative analysis, only spectra that have been defined by the user beforehand and stored, e .g., in a dye database, are used.

The algorithm searches these predefined dye spectra for the examples (i.e., dyes) that most closely match the fluorescence signal measured in a spectrally resolved manner and accordingly defines the reference spectra. The reference spectra obtained in this way and the lambda stack are then used as input parameters for a quantitative analysis, which again results in a color-coded image.

Applications of Dyes with Shifts in the Emission Centroid

Emission ratio dyes are used in different biomedical applications, for example, to determine ion concentrations and metabolite concentrations or changes therein, e.g., in cellular compartments or solutions.

The reversible interaction with the specific bonding partner (ligands such as $Ca^{2+}$. $Mg^{2+}$, $H^+$) results in a spectral shift of the fluorescence emission of these dyes (Indo-1, SNARF; Molecular Probes, Inc.). In general, two states of the dye, $F_F$ (free dye) and $F_B$ (dye with bonded ligands) (FIG. 15a), contribute to the emission spectrum measured at a given time in the observation volume, their relative proportions in a given volume being characterized in turn by the affinity between the dye and ligand described by the dissociation constant ($K_D$). Accordingly, the ratio of the fluorescences of $F_F$ and $F_B$ is a measure of the concentration of the ligand. The method described above can be applied in that the emission, spectra (FIG. 15b) associated with the bonding states $F_F$ and $F_B$ in the investigated biological system (in vivo) or in solutions (in vivo) are determined by means of the arrangement described above and by the ROIs to be determined by the user. For ion-sensitive emission ratio dyes, this is achieved, e.g., by adjusting ion-free or saturation conditions. The reference spectra can also be determined by means of a qualitative analysis. In this case, it is advantageous that the quantity of dye components (in method 2, described above, components $F_F$ and $F_B$ corresponding to FIG. 15a) is predetermined by the user. These reference spectra can be used for calculating the contribution of the dye states ($F_F$ and $F_B$) to the fluorescence emissions in the image points of a lambda stack or a series of lambda stacks acquired at different points in time or in different specimen planes by means of quantitative analysis (e.g., linear unmixing algorithms) (FIG. 9). Subsequent pixel-for-pixel division of the signals that are classified in two different image channels gives a sublinear measurement—independent of the dye concentration—of the ligand concentration R (ratio; FIG. 10), its spatial distribution and/or time dynamics. Absolute concentrations (equation calibration, titration calibration) can be determined from the values R based on in vitro or in vivo calibrating data which were ascertained with the respective emission ratio dye and known ligand concentrations.

For example, mixtures of two dyes (1) which interact with the same ligands, (2) whose emission centroids differ but do not change with the ligand bonding, and (3) whose fluorescence quantum yields change in an opposite manner depending on the ligand bonding (e.g., Fluo-3 and Fura Red; Molecular Probes, Inc.) can also be used in a corresponding manner according to the described method.

FRET (Fluorescence Resonance Energy Transfer) is the radiationless transfer of photon energy from an excited fluorophore (the donor) to another fluorophore (the acceptor). Prerequisites include overlapping of the donor emission spectra and acceptor excitation spectra and a close spatial association of the donor and acceptor. In biomedical applications, the FRET effect is used, e.g., to determine and track ion concentrations or metabolite concentrations ($Ca^{2+}$, cAMP, cGMP) or other, e.g., ligand-dependent structural changes (e.g., phosphorylation state of proteins, conformation changes of DNA). This is achieved by coupling the FRET partners, donor and acceptor (e.g., the synthetic fluorochromes FITC and rhodamine or the genetically coded fluorescing proteins CFP and YFP), in a molecule which undergoes changes in its secondary structure due to specific interaction with the ions, metabolites or ligands to be observed (example, Miyawaki, et al., Proc Natl Acad Sci USA 96, 2135–2140, March 1999; FIG. 17) or in one of two molecules which interact permanently or depending on environmental conditions. FIG. 16 shows the emission spectrum for the FRET partners for different distances between the donor and acceptor (a—great distance, no FRET/b—small distance, FRET interaction). In both cases, differences in the proportions of the free FRET system and ligand-bonded FRET system in the observation volume are connected with spectral differences in the fluorescence emission of the FRET system. In preferred excitation of the donor fluorescence, increases or decreases in the ligand bonding are expressed as opposite changes in amplitudes of the fluorescence emissions of the two FRET partners (FIG. 16).

One use of the method described herein, e.g., for the FRET measurements mentioned above, is irradiation of the specimen with light near the excitation optimum of FRET partner 1 (donor excitation, $\lambda_1$). The spectral range detected on the multichannel detector in the form of a lambda stack or a series of lambda stacks (Z or t) comprises the emission ranges of both FRET partners (FIG. 18, drawing part 1a). The behavior of the spectral signatures over time can be made visible (drawing part 1b) by defining ROIs (see above).

The fluorescence signals acquired as lambda stacks are then subjected to quantitative analysis (e.g., linear unmixing analysis) (FIG. 18, drawing part 2). The reference spectra required for this can be determined initially, e.g., in preparations or solutions containing only one of the FRET partners (in vivo or in vitro) by recording a lambda stack in the excitation wavelength ($\lambda_1$, donor excitation) and using the ROI function (see above and FIG. 9). By defining ROIs in the channels resulting from the quantitative analysis, it is possible to display the fluorescence intensities of the FRET partners and their changes over time graphically. Dividing the two image channels resulting from the quantitative analysis (unmixing analysis or PCA) by pixel gives images whose pixel values represent measurements of the fluorescence resonance energy transfer or FRET system ligand interaction (FIG. 18, drawing part 3) and, eg., the ion concentrations, metabolite concentrations and ligand concentrations to be observed can be calculated based on suitable calibration data (titration calibration, and so on).

Another application of the method described above consists in the separation of signals which are not relevant for the respective investigation or which interfere with the analysis. These signals can be, e.g., background light, autofluorescence, backscattered excitation light or room light. When the spectral distribution of these signals is initially determined in control preparations which are not further dyed (autofluorescence, backscattered excitation light) or in the absence of the preparation (background light, room light), the obtained spectra can be included in the linear unmixing analysis like the reference spectra of the dyes to be investigated (FIGS. 9 and 10). After unmixing, they are accordingly allocated to a separate image channel and separated from the signals to be investigated which can accordingly be observed separately.

Summary Clarifications of Terminology:

λ-Stack

Spectral distribution per image point, measured by the detection channels with dispersive splitting of the detected radiation, stored in storage elements with allocation to at least one additional (image point) coordinate x, y and/or z and/or measurement time t.

Quantitative Analysis

The contribution (proportion) of each spectral signature to the total signal (e.g., fluorescence signal) coming from the specimen is calculated for every image point (unmixing method). The calculation is carried out based on reference spectra which characterize the spectrum of the individual spectral signatures (e.g., dyes) and which have been stored in a database, generated from the image (ROI) or generated by qualitative analysis (PCA).

What is claimed is:

1. A method for investigating specimens for the operation of a laser scanning microscope or a fluorescence screening arrangement or a flow cytometer, the method comprising the steps of:

spectrally splitting a radiation coming from the specimen for specimen points or point distributions;

generating a λ-stack from the spectrally split radiation, which includes:

measuring the spectral distribution of the spectrally split radiation by individual detection channels of a detector; and storing signals correlated to detection signals of the detection channels with at least one of spatial coordinates x, y or z and/or correlated to a measurement time t.

2. The method according to claim 1, wherein a plurality of image channels allocated by color or spectral region and color correlation of false color images are generated.

3. The method according to claim 1, wherein region of interests (ROIs) are marked as relevant specimen areas by means of an input device or automatically.

4. The method according to claim 3, wherein the ROIs are used to form reference spectra.

5. The method according to claim 2, wherein a color-coded image is generated by superimposing the plurality of image channels when a plurality of dyes are contained in a relevant specimen area.

6. The method according to claim 3, wherein the ROIs are marked as relevant specimen areas by an input device, reference spectra are formed from the ROIs and a color-coded image is generated from the reference spectra by quantitative analysis.

7. The method according to claim 3, wherein the ROIs are marked as relevant specimen areas by means of an input device and a quantitative analysis is carried out by means of reference spectra from a stored database.

8. The method according to claim 3, wherein a qualitative analysis is carried out and relevant specimen areas are formed as the ROIs which are used for forming and storing reference spectra.

9. The method according to claim 1, wherein an input device is provided for selecting dyes which are quantitatively analyzed by means of a dye database and are displayed.

10. The method according to claim 9, wherein the dye database is generated by marked ROIs.

11. The method according to claim 2, wherein a ratio of the spectral components is formed from a color-coded image formed by superposition of the plurality of image channels for determining the ion concentrations.

12. The method according to claim 1, wherein the image channels or detection channels corresponding to unwanted signals such as autofluorescence or reflection or nonspecific fluorescence are eliminated.

13. The method according to claim 6, wherein the λ-stacks corresponding to the measured spectral distribution with individual detection channels are calculated from the stored color-coded image and the reference spectrum.

14. The method according to claim 3, wherein additional images are formed and/or the ROIs are marked and evaluated from these λ-stacks.

15. The method according to claim 1, wherein the spectral width of the detection within which the spectral distribution is detected collectively and to which an image channel is allocated is variable.

16. The method according to claim 3, wherein the spectra are evaluated in the ROIs.

17. The method according to claim 1, wherein adjusting elements are provided for adjusting the spectral width.

18. The method according to claim 17, wherein the adjusted spectral width is generated by digital signal combination or electronic combination of detection channels.

19. The method according to claim 17, wherein adjusting elements and the spectral width are displayed on a monitor in such a way that the adjusting areas of the adjusting elements are spatially correlated to the spectral width.

20. The method according to claim 1, wherein sliders are provided, whose position on the monitor corresponds to the position of an associated spectral region.

21. The method according to claim 17, wherein an adjusted wavelength is indicated by adjusting the pointer of a computer mouse on the adjusting element, and the adjusted wavelength area is indicated on the monitor by adjusting between two adjusting elements.

22. The method according to claim 1, wherein a wavelength-dependent display of the temporal behavior of specimen areas or of the entire specimen is carried out on a monitor.

23. The method according to claim 1, wherein a gray scale image is generated from the λ-stack in that the maximum intensity value is determined and displayed for every x,y pixel position over the wavelength regions.

24. The method according to claim 23, wherein, every pixel is characterized by the color which corresponds to the mean wavelength of the wavelength region from which the brightest pixel of the λ-stack originates.

25. The method according to claim 1, wherein the individual images of the λ-stack are displayed on a screen at least partially in series so as to overlap adjacent to one another or one behind the other.

26. The method according to claim 1, wherein time-dependent and/or z-dependent views are also generated and displayed in addition to an x,y λ-stack display.

27. The method according to claim 1, wherein the λ-stack is sectioned and the resulting section images are displayed.

28. The method according to claim 1, wherein quantitative analysis involves an unmixing process.

29. The method according to claim 28, wherein the qualitative analysis involves a quantative analysis process.

* * * * *

UNITED STATES PATENT AND TRADEMARK OFFICE
CERTIFICATE OF CORRECTION

PATENT NO. : 7,009,699 B2  Page 1 of 1
APPLICATION NO. : 10/057571
DATED : March 7, 2006
INVENTOR(S) : Ralf Wolleschensky et al.

It is certified that error appears in the above-identified patent and that said Letters Patent is hereby corrected as shown below:

<u>TITLE PAGE</u>

Third Inventor's name should read as follows:

Item [75]    Sebastian TILLE

Signed and Sealed this

Twenty-sixth Day of December, 2006

JON W. DUDAS
*Director of the United States Patent and Trademark Office*